United States Patent [19]

Mandle

[11] Patent Number: 4,566,790
[45] Date of Patent: Jan. 28, 1986

[54] CUVETTE ARRAY

[75] Inventor: Richard M. Mandle, Pompton Lakes, N.J.

[73] Assignee: Electro-Nucleonics, Inc., Fairfield, N.J.

[21] Appl. No.: 485,174

[22] Filed: Apr. 15, 1983

[51] Int. Cl.$^4$ ............................................. G01N 1/10
[52] U.S. Cl. .................................. 356/246; 250/576; 422/72; 422/102
[58] Field of Search ...................... 356/246, 422, 440; 250/576; 422/72, 102

[56] References Cited

U.S. PATENT DOCUMENTS

| 3,986,534 | 10/1976 | Schmidt | 356/246 X |
| 4,123,173 | 10/1978 | Bellock et al. | 422/64 X |
| 4,154,793 | 5/1979 | Guigan | 356/246 X |
| 4,226,531 | 10/1980 | Tiffany et al. | 250/576 X |
| 4,373,812 | 2/1983 | Stein et al. | 356/427 X |

Primary Examiner—Davis L. Willis
Assistant Examiner—Matthew W. Koren
Attorney, Agent, or Firm—Robert Scobey

[57] ABSTRACT

An improved cuvette array for a centrifugal analyzer is disclosed. The array is conventionally formed from upper and lower discs of flexible thermoplastic material, in which the lower disc is formed with a plurality of compartments circumferentially spaced about a first central hub, and the upper disc is bonded to the outer periphery of the lower disc and closes an outer peripheral portion of the compartments. The array is improved by forming the upper disc with a central portion that includes a second central hub positioned above the first central hub, together with an intermediate web that bridges the second central hub to the outer peripheral portion of the upper disc so as to close off the inner peripheral portion of the compartments. The intermediate web portion may be joined to the outer peripheral portion of the upper disc by a tearible score line to permit the central portion of the upper disc to be entirely removed.

4 Claims, 5 Drawing Figures 4,566,790

CUVETTE ARRAY

BACKGROUND AND BRIEF DESCRIPTION OF THE INVENTION

This invention relates to cuvette arrays for centrifugal analyzers. The particular object of the invention is to provide a cuvette array which is simple to manufacture and simple to use. The invention is an improvement of the cuvette array disclosed in U.S. Pat. No. 4,123,173 which issued Oct. 13, 1978.

In U.S. Pat. No. 4,123,173, the cuvette array there disclosed is formed from upper and lower discs of flexible thermoplastic material, in which the lower disc is formed with a plurality of compartments circumferentially spaced about a central hub, and the upper disc is bonded to the outer periphery of the lower disc to close off an outer peripheral portion of the compartments. The inner peripheral portion of those compartments has been left exposed in the disc, and hence evaporation of reagents in those inner peripheral compartment portions may occur in a disc. In the past, it has been the practice to separately form a centering piece for the cuvette array, which is positioned over the central hub abovementioned to enable the nesting of one cuvette array over another, while at the same time preventing relative rotation of the nested arrays so as to prevent scratching of the arrays which might occur upon relative movement thereof during shipping.

The present invention simplifies the construction of a cuvette array by eliminating a separately formed centering piece and, instead, integrally forming a centering piece with the upper disc during the fabrication of the latter. Furthermore, by integrally forming such a centering piece, so that it is co-extensive with the outer peripheral portion of the upper disc, evaporation of reagent which might take place from the open compartments of the array disclosed in the cited U.S. Patent is avoided. The new central portion which is integrally formed into the upper disc of the array may be so formed with a tearible score line to permit the central portion to be entirely removed, if desired, to permit the washing of the cuvette compartments and re-use of the array.

The invention will be more completely understood by reference to the following detailed description, taken in conjunction with the appended drawings.

DETAILED DESCRIPTION

Figure 1:
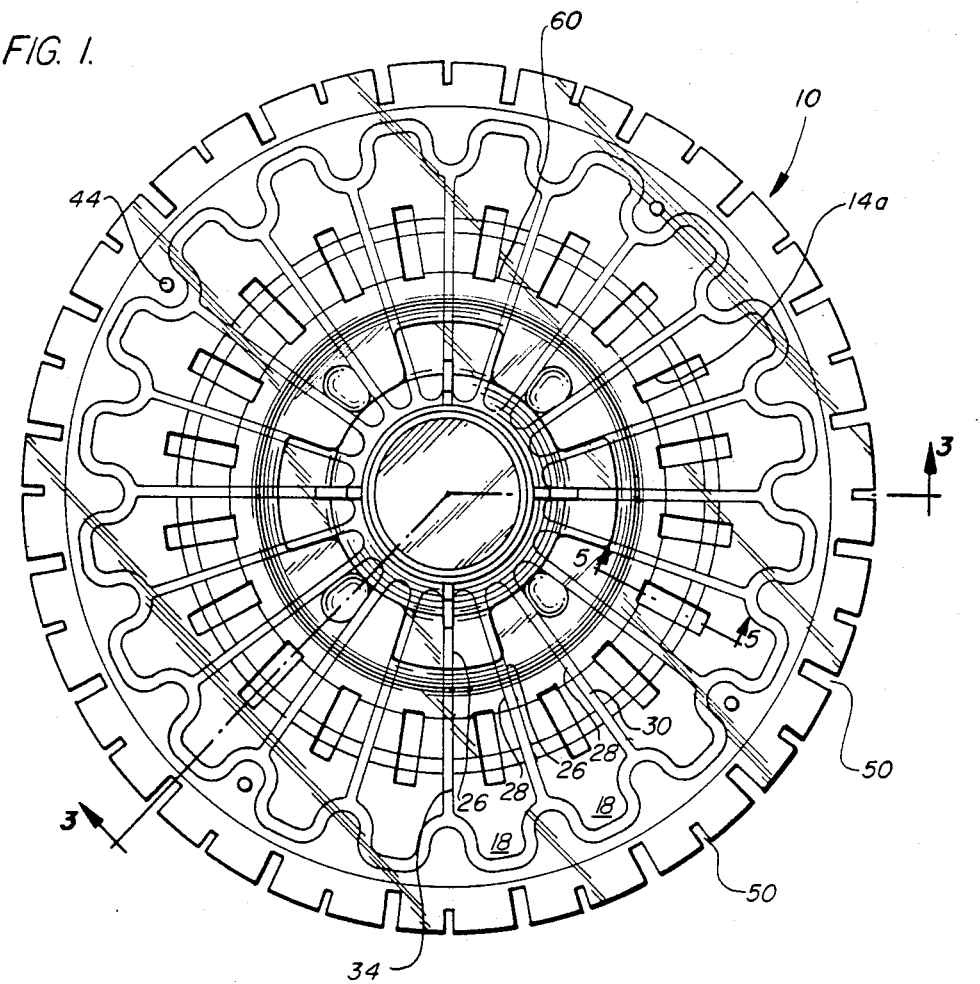
FIG. 1 is a plan view of a cuvette array embodying the invention.
Figure 2:
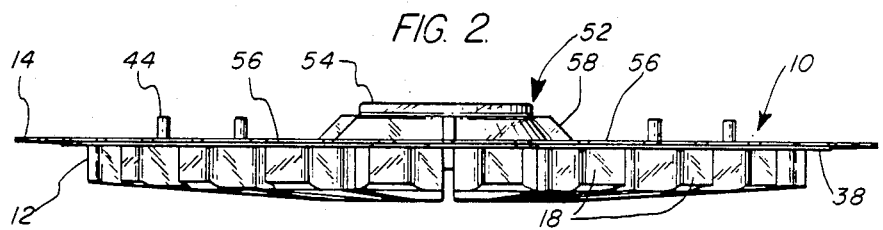
FIG. 2 is a side view of the array of FIG. 1.
Figure 3:
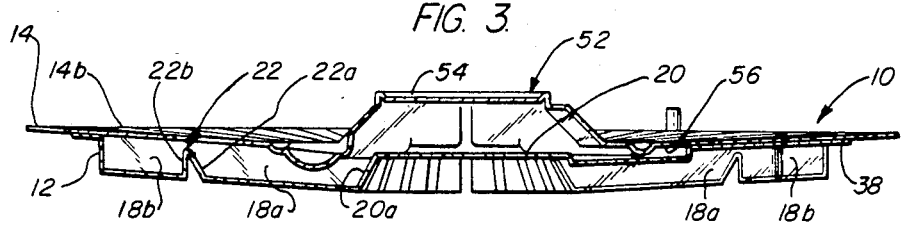
FIG. 3 is a sectional view of the array of FIG. 1, taken along the section 3—3 in FIG. 1.
Figure 4:
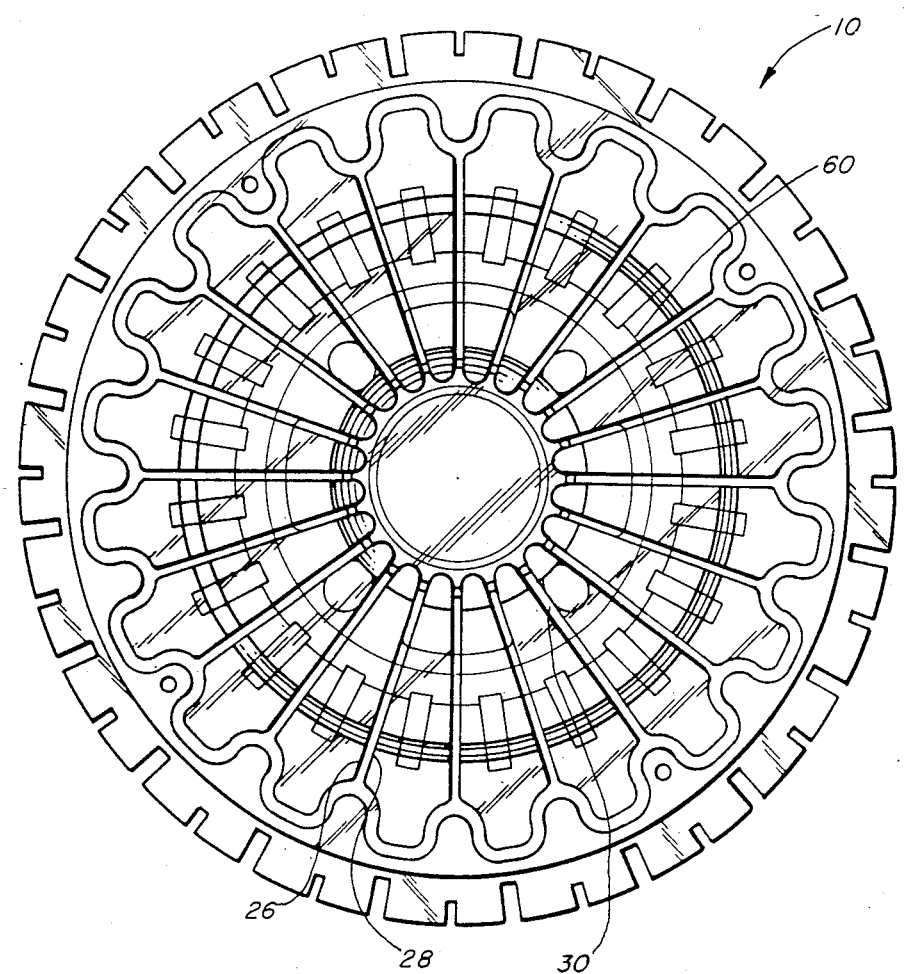
FIG. 4 is a bottom view of the array of FIG. 1.

Referring to FIGS. 1 to 4, a cuvette array 10 is shown. The array is formed from flexible thermoplastic material, and includes a lower disc 12 and an upper disc 14. The discs are preferably formed from polyvinyl chloride, which is particularly useful, since it is inert to most fluids used for test purposes, it is of good light transmissivity for the proper transmission of light therethrough during a test, and is of sufficient strength to retain its configuration while undergoing forces created during rotation of the cuvette assembly. Typically thermoplastic material in sheet form is utilized, which may be thermoformed into the configuration of the upper and lower discs.

The lower disc 12 is formed into a plurality of compartments 18. These compartments 18 are circumferentially spaced about a first central hub 20, and extend outwardly in the radial direction. The compartments 18 constitute a series of radially inner compartments 18a and a series of radially outer compartments 18b. Each radially inner compartment 18a communicates with an individual one of the radially outer compartments 18b, and is separated therefrom by dividing wall structure 22, which includes an inclined wall 22a and a vertical wall 22b. The central hub 20 bounds the inner periphery of the compartments 18 by inclined wall structure 20a.

Each compartment 18 includes side walls 26 and 28. The adjacent side walls 26, 28 of adjacent compartments 18 are spaced apart from each other, as at 30, and are joined together by flat sections of thermoplastic material 34. The lower disc 12 terminates in an outer circumferential flange 38 which is coplanar with the flat section 34 of the lower disc structure which joins together the adjacent side walls 26, 28. The upper disc 14 is bonded to the lower disc 12 in the regions of these flat sections 34 and outer flange 38. The bonding together of the two discs may be by radio frequency heat sealing, for example, and the sealing as shown isolates adjacent compartments 18 from each other, preventing undesirable crossover of fluid from one compartment to another.

The upper disc 14 is also typically produced by stamping from thermoplastic sheet material. The upper disc 14 closes off the compartments 18, but includes cut-away portions 14a thereof in registry with the compartments 18. In particular, the cutaway portions 14a extend radially over both compartment sections 18a and 18b for the purpose of introducing fluids into those compartments. The upper disc is also slotted, as at 50, for signal processing purposes.

To aid in positioning the upper disc 14 with respect to the lower disc 12 prior to the bonding together of the two discs, nipples 44 may be employed forming a part of the lower disc 12. There are four of such nipples 44 shown in FIG. 1, although this number is representative, and they are equiangularly spaced about the periphery of the lower disc 12. The upper disc 14 includes corresponding holes therein which register with the nipples 44 and provide proper registry of the upper and lower discs, particularly so that the cutaway portions 14a are positioned over the center regions of the compartments 18.

The upper disc 14 is formed with an integral central portion 52, that includes a central hub 54 that is positioned above the central hub 20 of the lower disc 12. The central portion 52 of the upper disc also includes an intermediate web 56 that bridges the central hub 54 to the outer peripheral portion 14b of the upper disc. In this fashion, the inner peripheral portions of the compartments 18a, which previously had been open to the atmosphere in the cuvette array disclosed in U.S. Pat. No. 4,123,173 are now closed, thereby preventing evaporation of fluids from those compartments.

The central hub 54 of the upper disc 14 is formed with indexing ribs 58 thereon, which engage corresponding channels in the lower disc of another cuvette array that is nested on top of the present array, to restrain the two nested arrays from relative rotation in the nested condition. In particular, the channels referred to are the spaces 30 between adjacent walls 26, 28 of adjacent compartments 18 (present in the lower disc 12 and accessible from the underside of a lower disc).

Figure 5:
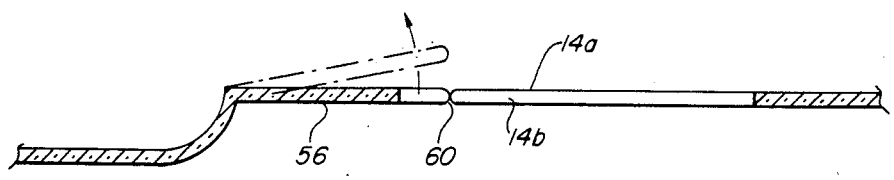
FIG. 5 is an enlarged sectional view of a portion of the array of FIG. 1, taken along the section 5—5 in FIG. 1.

Additionally, the intermediate web portion 56 of the upper disc 14 is joined to the outer peripheral portion 14b of the upper disc by a tearible score line 60 to permit the central portion 52 of the upper disc with its central hub 54 and intermediate web 56 to be entirely removed from the assembly as desired. Such removal may be desired in order to re-use the array, e.g., wash, rinse, and dry all compartments 18a, with subsequent re-use of the array for further testing. FIG. 5 shows how the intermediate web 56 may be torn about the tearible score line 60 to separate that web from the outer peripheral portion 14b of the upper disc.

It will be appreciated that a unique cuvette array has been described. The preferred embodiment disclosed above is subject to modification by those skilled in the art. Accordingly, the invention should be taken to be defined by the following claims.

I claim:

1. In a cuvette array for a centrifugal analyzer in which the array is formed from upper and lower discs of flexible thermoplastic material, the lower disc is formed with a plurality of compartments circumferentially spaced about a first central hub, and the upper disc is bonded to the outer periphery of the lower disc and closes off an outer peripheral portion of said compartments, the improvement wherein said upper disc is formed with a central portion that includes a second central hub positioned above said first central hub, and an intermediate web that bridges said second central hub to the outer peripheral portion of the upper disc so as to close off the inner peripheral portion of said compartments, and in which said second central hub is formed with indexing ribs thereon to engage corresponding channels in the lower disc of another cuvette array that is nested on top of the first-mentioned array, to restrain said arrays from relative rotation in the nested condition.

2. A cuvette array as in claim 1, in which said intermediate web portion is joined to said outer peripheral portion of said upper disc by a tearible score line to permit said central portion of said upper disc with its second central hub and intermediate web portion to be entirely removed.

3. A cuvette array as in claim 1, in which said compartments of said lower disc include side walls, the side walls of adjacent compartments are spaced from each other, and said channels are defined by the spaces between the side walls of adjacent compartments.

4. In a cuvette array for a centrifugal analyzer in which the array is formed from upper and lower discs of flexible thermoplastic material, the lower disc is formed with a plurality of compartments circumferentially spaced about a first central hub, and the upper disc is bonded to the outer periphery of the lower disc and closes off an outer peripheral portion of said compartments, the improvement wherein said upper disc is formed with a central portion that includes a second central hub positioned above said first central hub, and an intermediate web that bridges said second central hub to the outer peripheral portion of the upper disc so as to close off the inner peripheral portion of said compartments, in which said intermediate web portion is joined to said outer peripheral portion of said upper disc by a tearible score line to permit said central portion of said upper disc with its second central hub and intermediate web portion to be entirely removed.

* * * * *